(12) United States Patent  
Amann

(10) Patent No.: US 7,833,308 B2
(45) Date of Patent: Nov. 16, 2010

(54) FILTER ASSEMBLY WITH MULTIPLE INLETS AND MULTIPLE FILTER MEMBERS

(75) Inventor: Michael A. Amann, St. Louis, MO (US)

(73) Assignee: Home Health Medical Equipment, Inc., St. Louis, MO (US)

( * ) Notice: Subject to any disclaimer, the term of this patent is extended or adjusted under 35 U.S.C. 154(b) by 289 days.

(21) Appl. No.: 12/022,287

(22) Filed: Jan. 30, 2008

(65) Prior Publication Data

US 2009/0188217 A1 Jul. 30, 2009

(51) Int. Cl.
*B01D 46/00* (2006.01)
(52) U.S. Cl. .............................. 55/484; 55/521; 96/381
(58) Field of Classification Search ............ 55/482, 55/484, 323, 324, 502, 521, DIG. 31, 483; 96/380, 381, 383
See application file for complete search history.

(56) References Cited

U.S. PATENT DOCUMENTS

| | | | |
|---|---|---|---|
| 3,289,847 A | 12/1966 | Rothemund | |
| 4,036,616 A | 7/1977 | Byrns | |
| 4,063,913 A | 12/1977 | Kippel et al. | |
| 4,493,717 A | 1/1985 | Berger, Jr. et al. | |
| 4,588,426 A | 5/1986 | Virgille et al. | |
| 5,024,764 A | 6/1991 | Holler | |
| 5,223,011 A * | 6/1993 | Hanni | ................. 55/484 |
| 5,250,179 A | 10/1993 | Spearman | |
| 5,290,445 A | 3/1994 | Buttery | |
| 5,376,270 A | 12/1994 | Spearman | |
| D357,737 S | 4/1995 | Spearman | |
| 5,454,945 A | 10/1995 | Spearman | |
| 5,512,074 A * | 4/1996 | Hanni et al. | ................. 55/484 |
| 5,524,585 A * | 6/1996 | Conoscenti | ............. 123/198 E |
| 5,536,285 A * | 7/1996 | Isaksson et al. | ............. 55/302 |
| D373,637 S | 9/1996 | Spearman | |
| 5,599,448 A | 2/1997 | Spearman | |
| D410,727 S | 6/1999 | Khamis et al. | |
| 5,916,435 A | 6/1999 | Spearman et al. | |
| 6,482,247 B2 * | 11/2002 | Jaroszczyk et al. | ............. 55/484 |
| 6,702,880 B2 | 3/2004 | Roberts et al. | |
| 6,835,224 B2 * | 12/2004 | Cheng | ................. 55/428 |
| 6,866,700 B2 | 3/2005 | Amann | |
| 7,141,101 B2 | 11/2006 | Amann | |
| 7,540,895 B2 * | 6/2009 | Furseth et al. | ............. 55/385.3 |
| 7,601,209 B1 * | 10/2009 | Gunderson et al. | ............. 96/387 |
| 2004/0261621 A1 | 12/2004 | Lindsay | |
| 2007/0186520 A1 | 8/2007 | Amann | |

* cited by examiner

*Primary Examiner*—Michael A Marcheschi
*Assistant Examiner*—Robert A Clemente
(74) *Attorney, Agent, or Firm*—Husch Blackwell LLP

(57) ABSTRACT

The present invention discloses a filter assembly which includes a compartmented housing structure having a plurality of inlets and an outlet. A first inlet is positioned in flow communication with a first chamber portion and a first filter member. A second inlet is positioned in flow communication with a second chamber portion and a second filter member. A third chamber portion is located between the first and second filter members and is in flow communication with the outlet such that ambient air entering the housing through the first and second inlets will flow through the first and second filter members into the third chamber portion and through the outlet.

20 Claims, 3 Drawing Sheets

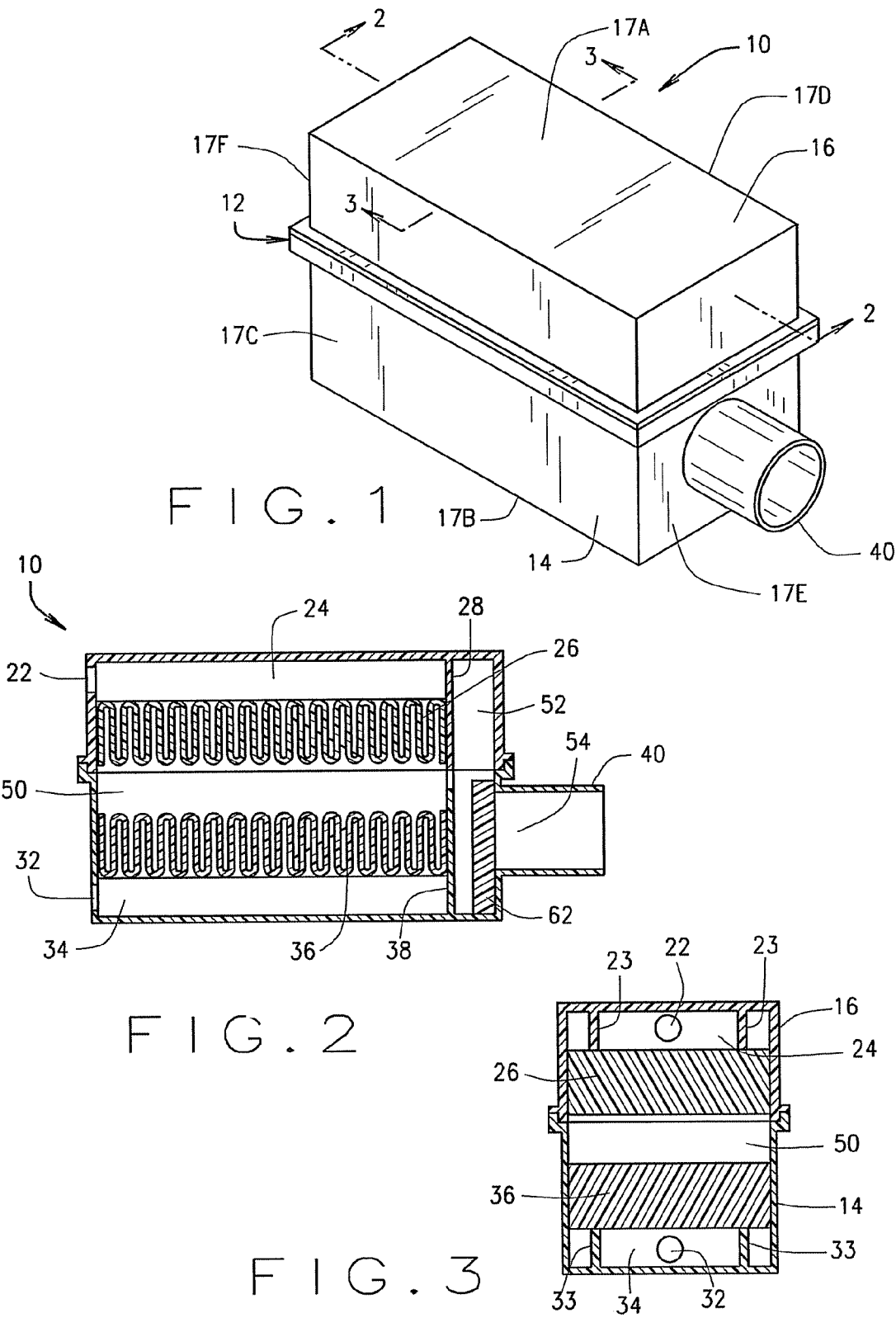

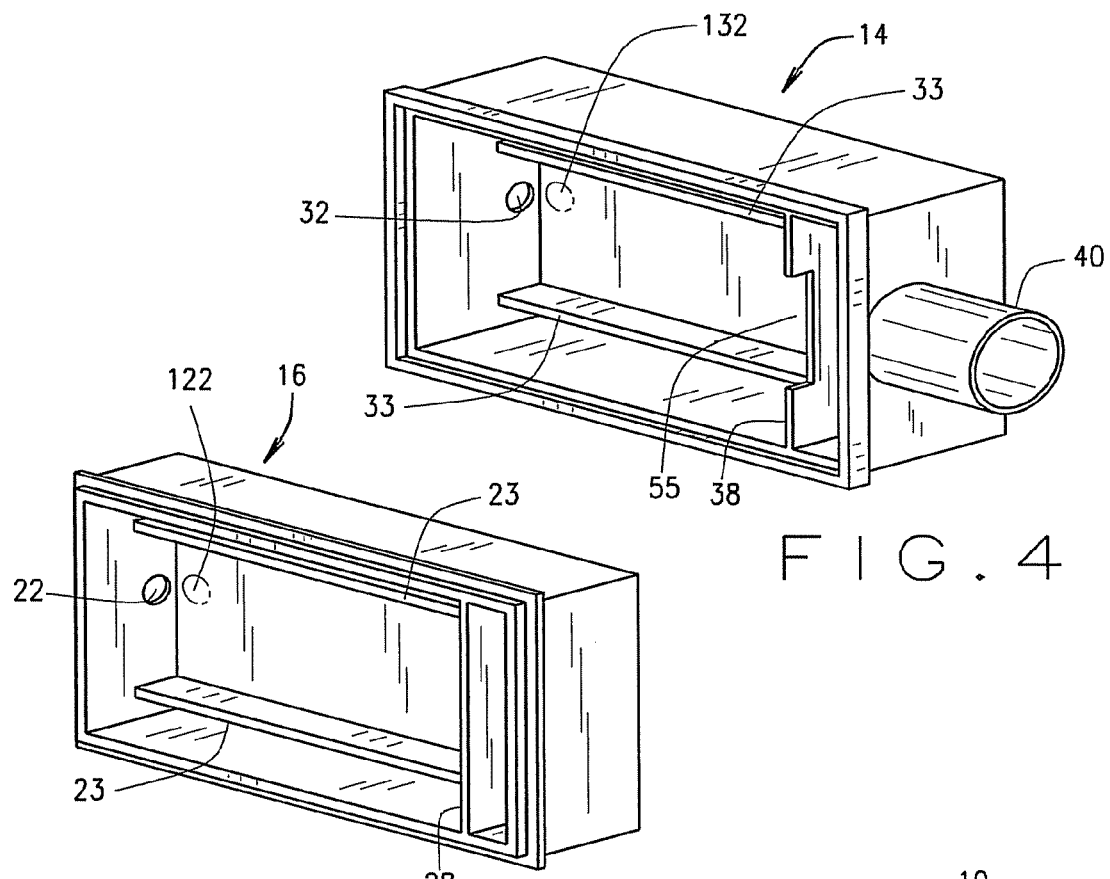
FIG. 4
FIG. 5
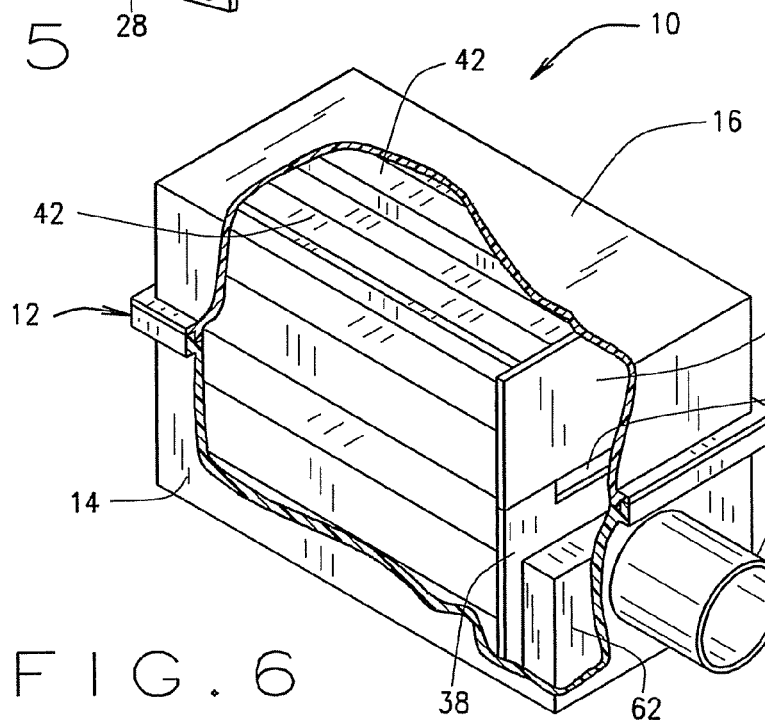
FIG. 6

FILTER ASSEMBLY WITH MULTIPLE INLETS AND MULTIPLE FILTER MEMBERS

BACKGROUND OF THE INVENTION

This invention relates generally to filter assemblies and, more particularly, to various embodiments of a filter assembly configured for use with an air flow inducing device utilized in oxygen concentrators and other medical devices in the health care medical equipment industry.

Oxygen concentrators are commonly used in the care of respiratory patients, particularly, in the health care environment, to provide sufficiently high concentration of oxygen to the patient without having to use high pressure tanks or liquid oxygen. Oxygen concentrators utilize ambient atmospheric air as their source of oxygen in conjunction with a separation system such as one or more molecular sieve beds to separate oxygen from the other gases found in the air and to provide that oxygen in concentrated form to the patient. Atmospheric air typically includes approximately 80% nitrogen and 20% oxygen. In one form of separator, nitrogen is absorbed by an absorption system and is retained therein until subsequently purged. However, the concentrator and other medical devices tend to be subject to increased wear from atmospheric particles which can flow into the system, thereby decreasing the service life of the machinery, while increasing maintenance time and expense.

Typically, these issues are dealt with by a filter used in the in-feed air stream of the concentrator to filter particles and to protect the concentrator from particles and the patient from certain bacteria present in the atmosphere. HEPA filters are commonly used in these applications, and they are rated to remove 99.97% of the particles 0.3 µm or larger. These filters typically employ a large surface area (about 120 square inches of surface filtration area) and provide a long service life. Ambient air is drawn into an oxygen concentrator from the ambient environment. Such ambient air is then passed through a filter assembly to remove dust and other contaminants, and the filtered air is then pressurized by a compressor for introduction into the absorption system. Once the compressed air is introduced into the absorption system, the nitrogen is selectively absorbed and released to atmosphere leaving the residual oxygen available for patient use. The absorption system is then regenerated and made ready for the next cycle. Oxygen concentrators typically produce an oxygen concentration usually in the range of 90-95% by volume.

Use of an effective filtration system for separating contaminants from any gas is important for a multitude of reasons. Properly and effectively filtering the incoming ambient air before it is compressed and introduced into the absorption system of an oxygen concentrator is likewise important because effective filtration not only improves the overall efficiency of the oxygen concentrator but it also improves and increases the oxygen concentration provided to the patient. Poor filtration of the incoming air also subjects the oxygen concentrator and its associated compressor to increased wear from particles which enter the system thereby decreasing service life while increasing maintenance.

Filtration area is one factor for evaluating the performance of a filter apparatus. The size and overall configuration of the filter housing associated with a particular oxygen concentrator generally determine the maximum filtration area. However, the larger the filtration area with the same footprint of the filter housing is preferred for higher performance of the filter apparatus.

It is therefore desirable to provide a filter assembly which improves the air filtration performance to the absorption system of an oxygen concentrator or other compressor assembly, and which includes means for improving the filtration capacity and life of the filter assembly.

Prior art filters for use in an oxygen concentrator have been disclosed with features such as noise attenuation and easy replacement. For example, a filter with a single inlet is disclosed in Roberts et al, U.S. Pat. No. 6,702,880 entitled Inlet Silencer/Filter For An Oxygen Concentrator. The inlet silencer/filter for an oxygen concentrator includes a HEPA filter and an adjoining chamber for receiving air flow after passing through the HEPA filter. The chamber is defined on one face by the HEPA filter, and by sound absorbing padding on at least four (4) other faces. Air is directed from the HEPA filter, through the open chamber and then through the sound absorbing padding by a flow deflector plate. Air flows from here through air channels and into an open chamber leading to an outlet from the air silencer/filter. However, the amount of air passing through the single inlet associated with a filter member is limited.

Another filter is disclosed in Amann U.S. Pat. No. 7,141,101 entitled Filter Assembly With Noise Attenuation (Amann '101), which patent is owned by the present Assignee. Amann '101 discloses a filter assembly including a compartmented housing having an inlet opening, a single inlet chamber, an outlet opening, a filter member, and a plurality of noise attenuating members located therewithin. The configuration of the compartmented housing in conjunction with the positioning and location of the filter member and the noise attenuating members therewithin all contribute to dampen and dissipate sound waves generated within the housing due to air flow movement therethrough. However, the amount of air passing through the single inlet and inlet chamber associated with a filter member needs to be increased.

Amann U.S. Pat. No. 6,866,700 entitled Filter Housing Assembly For Use in Oxygen Concentrators and Other Compressors (Amann '700), which patent is likewise owned by the present Assignee, discloses a substantially frusto-conical shaped filter housing member having one or more inlet openings associated with a substantially closed dome shaped portion. Ambient air entering the one or more inlet openings flow through a single inlet chamber before passing through a substantially cylindrically shaped filter member and exiting through a single outlet opening. In this particular filter assembly, air travels from the outside of the filter member through the filter member to a central passageway extending through the interior portion of the filter member. Once the air has traveled to this interior passageway, it then flows through this interior passageway to the outlet opening for passage into a compressor assembly.

Accordingly, the present invention is directed to a filter assembly which overcomes one or more of the problems as set forth above.

BRIEF SUMMARY OF THE INVENTION

The present invention overcomes many of the shortcomings and limitations of the prior art devices discussed above and teaches the construction and operation of several embodiments of a filter assembly adapted for use in a wide variety of different compressor assemblies wherein air is filtered such as for use in oxygen concentrators and other medical applications in the home care medical equipment area. In one aspect of the present invention, the filter assembly includes a compartmented housing structure having a plurality of inlets and at least one outlet. The inlets are positioned in the walls of the housing for allowing ambient air to enter the housing for passage through a filter element separating an inlet chamber portion from an outlet chamber portion before becoming compressed for use in an oxygen concentrator or other compressor application. At least two of the inlets have separate inlet chamber portions, respectively. A first inlet is positioned in flow communication with a first inlet region or first inlet chamber portion in the housing which includes a first filter member such as a solid core type filter, a pleated type filter, a HEPA filter, or other filter element, and which may optionally include a noise attenuating foam member positioned adjacent the first filter member. A second inlet is positioned in flow communication with a second inlet region or second inlet chamber portion in the housing which includes a second filter member, and which may also optionally include a noise attenuating foam member positioned adjacent the second filter member. Each of the first and second chamber portions can be positioned in flow communication with a plurality of inlet openings, respectively. The housing structure of the filter assembly also includes a third chamber portion. The third chamber portion is located between the first filter member and the second filter member and in flow communication with the outlet such that ambient air entering the housing through the inlets will flow through the respective filters into the third chamber portion associated with the housing.

In another embodiment of the present invention, the third chamber portion is located between the first and second filter members and is in flow communication with an outlet region or outlet chamber portion in flow communication with the outlet. Another noise attenuating member can be optionally positioned at the mouth of the outlet to suppress the noise associated with the air flow as it passes through the third chamber portion and the outlet chamber portion and into the outlet.

Ambient air enters the housing through a plurality of inlets and travels through the first and second chamber portions in a manner as previously described. Air exiting the first chamber portion and second chamber portion enters the third chamber portion which includes the outlet. Once the air has traveled into the third chamber portion, it then flows through the third chamber portion and through the outlet thereby allowing the filtered air to exit the filter assembly for passage into the compressor assembly of an oxygen concentrator or other compressor device.

BRIEF DESCRIPTION OF DRAWINGS

FIG. 1 is a perspective view of a first embodiment of the present filter assembly constructed in accordance with the teachings of the present invention.

FIG. 2 is a cross-sectional view of the filter assembly of FIG. 1 taken along line 2-2 of FIG. 1.

FIG. 3 is a cross-sectional view of the filter assembly of FIG. 1 taken along line 3-3 of FIG. 2.

FIG. 4 is a perspective view of one housing portion of the filter assembly of FIG. 1.

FIG. 5 is a perspective view of another housing portion of the filter assembly of FIG. 1.

FIG. 6 is a cut-away perspective view of the filter assembly of FIGS. 1-5.

Figure 7:
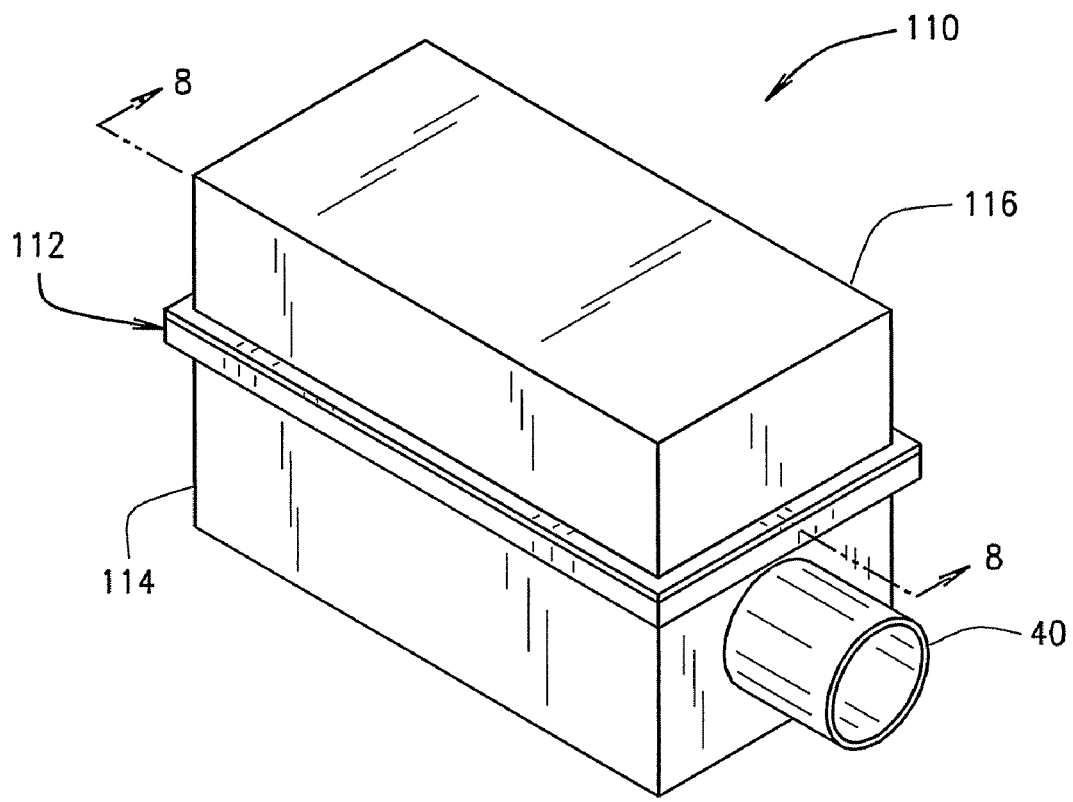
FIG. 7 is a perspective view of another embodiment of the present filter assembly constructed in accordance with the teachings of the present invention.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein. Like numbers utilized throughout the various Figures designate like or similar parts or structure.

DETAILED DESCRIPTION OF THE INVENTION

The filter assembly 10 includes a housing 12 with an interior chamber. The chamber is divided into a plurality of chamber portions at least partially by filter members or filter segments, hereinafter filter members for brevity. There are at least two inlet chamber portions and at least one outlet chamber portion with filter material separating the same. Each inlet chamber portion has a respective inlet opening and the outlet chamber portion has an outlet opening. The inlet openings are positioned remote from the outlet opening so incoming air can flow over a substantial portion of the filter members in a direction generally toward the outlet opening.

Referring to the drawings more particularly by reference numbers, the numeral 10 in FIGS. 1, 2 and 6 identifies one embodiment of a filter assembly constructed according to the teachings of the present invention. The filter assembly 10 can be constructed so as to be compatible for attachment to any suitable type of compressor fitting associated with any compressor assembly where the present filter assembly may be utilized. Although the specific air flow device discussed herein is directed to an oxygen concentrator, particularly useful in the medical equipment industry, it is pointed out that the present filter assembly can be utilized with any compressor assembly where ambient air or any other air source is to be filtered for the compression process or other application.

The filter assembly 10 illustrated in FIGS. 1 and 6 includes a generally hollow rectangularly shaped housing 12 which, for ease of manufacture, includes two separate housing portions, namely, a lower housing portion 14 illustrated in FIG. 4 and an upper housing portion 16 illustrated in FIG. 5. As used herein, upper, lower and other position terms are used to describe the invention as oriented in the drawings. Orientation terms, as used herein, are for orientation of the filter assembly as oriented in FIGS. 1 and 2. Housing portions 14 and 16 are preferably bonded or otherwise securely attached to each other to form an airtight seal at the seam using any suitable means. It has been found that an ultrasonic weld joint accomplishes this task when the housing 12 is polymeric, although other attachment or bonding means can likewise be utilized so long as an airtight seal is formed. As shown, the housing 12 has six generally planar sides or walls 17A-17F which form a hollow rectangular solid with a chamber portion therein divided into chamber portions described below.

As best shown in FIGS. 2, 3, 4, 5 and 6, the upper housing portion 16 includes a first inlet opening 22, shown in the form of a circular opening, for allowing ambient air to enter the filter assembly for passage through the end wall of the upper housing portion 16. The first inlet opening 22 can be of any shape and is located in flow communication with a first inlet region or chamber portion 24 which provides for flow communication with a first filter member 26. The first filter member 26 separates the first chamber portion 24 from other chamber portions. The first filter member 26 can be a solid core type filter, a pleated type filter, a HEPA filter, or other appropriate filter depending upon the particular application involved. The first chamber portion 24 has projecting support members 23 extending between the top wall 17A of the upper housing portion 16 and the top portion of the first filter member 26 so as to form a channel or space in the first chamber portion 24 as shown in FIGS. 3 and 5 to provide support to the filter member 26 and to hold the filter member 26 spaced from the housing wall 17A. In another embodiment, a pair of noise attenuating members 42, as shown in FIG. 6 and as described in Assignee's U.S. Pat. No. 7,141,101, which disclosure is incorporated herein by reference, can be positioned in spaced apart relationship adjacent the top portion of the first filter member 26 so as to form a flow channel therebetween. The noise attenuating members 42 are preferably foam type members, although any noise attenuating means such as felt pads and the like may be utilized, and function as sound dampening means to dampen any sound generated within the housing due to air flow passing therethrough. The noise attenuating members 42 are optional and the present filter assembly 10 will function and operate equally well for filtering without such members. The first inlet opening 22 is located in flow communication with the first chamber portion 24 such that ambient air entering the opening 22 will flow through the first chamber portion 24 and through the filter member 26 into a third region or third chamber portion 50 located adjacent to and on the opposite side of first filter member 26.

The lower housing portion 14 includes a second inlet opening 32, shown in the form of a circular opening, for allowing ambient air to enter the filter assembly for passage through the end wall of the lower housing portion 14. The second inlet opening 32 can likewise be of any shape and is located in flow communication with a second inlet region or chamber portion 34 which provides for flow communication with a second filter member 36. The second filter member 36 separates the second chamber portion 34 from other chamber portions. The second filter member 36 can be a solid core type filter, a pleated type filter, a HEPA filter, or other appropriate filter depending upon the particular application involved. The second filter member 36 can likewise be of the same type as the first filter member 26, or the respective filter members 26 and 36 can be of different types. The second chamber portion 34 has projecting support members 33 similar to support members 23 extending between the bottom wall of the lower housing portion 14 and the bottom portion of the second filter member 36 so as to form a channel in the second chamber portion 34 as shown in FIGS. 3 and 4. In another embodiment, a pair of noise attenuating members can be positioned in spaced apart relationship adjacent the bottom portion of the second filter member 36 so as to form a flow channel therebetween (not shown). Here again, these noise attenuating members are optional. The second inlet opening 32 is positioned in flow communication with the second chamber portion 34 such that ambient air entering the opening 32 will flow through the second chamber portion 34 and through the second filter member 36 into the third chamber portion 50 located adjacent to and on the opposite side of the second filter member 36 and between the filter members 26, 36. Thus, according to the illustrated embodiment, the total surface area for filtration is doubled with the same footprint of the filter housing structure. The first chamber portion 24 is substantially separated from the second chamber portion 34 by the filter members 26, 36 and third chamber portion 50.

The first and second inlet openings 22, 32 are positioned remote from the outlet opening 52 so incoming air can flow over a substantial portion of the filter members 26, 36 in a direction generally toward the outlet opening 52. If an inlet opening 22, 32 is positioned close to the outlet opening 52, a reduced surface area of the filter members is used for filtration without reverse flow because ambient air entering the housing 12 would flow preferentially through only that portion of the filter members 26, 36 between the inlet openings 22, 32 and outlet opening 52. This can cause an early preferential clogging of portions of the filter member, and thus, a short service life of the filter members. It is pointed out that the present filter assembly can be utilized with more than one inlet opening which is positioned in flow communication with each chamber portion 24, 34. Such a plurality of inlet openings 22, 32 can be positioned anywhere along the length of the respective inlet chamber portions 24, 34 but at least one such opening for each inlet chamber portion should be positioned remote from the outlet opening 54 as described above. The inlet opening 22 of the upper housing portion 16 is positioned in the end wall of the upper housing portion 16 as illustrated in FIG. 5. In a further embodiment of the present invention, the inlet opening 122 can be positioned on the top side wall of the upper housing portion 16 as shown in dotted line form in FIG. 5. The inlet opening 32 of the lower housing portion 14 is positioned in the end wall of the lower housing portion 14 as illustrated in FIG. 4. In a further embodiment of the present invention, the inlet opening 132 can be positioned on the bottom side wall of the lower housing portion 14 as shown in dotted line form in FIG. 4. Other locations on the top and bottom side walls 17A and 17B of the housing 12 can likewise be used for positioning and locating the respective inlet openings 22, 32 depending upon the overall configuration of the filter assembly and the particular application involved. The inlet openings can also be positioned at certain locations on housing side walls 17C and 17D depending upon the particular configuration of the filter assembly.

As best shown in FIG. 6, the optional noise attenuating members 42 are positioned and held in place adjacent the first filter member 26. The noise attenuating members 42 serve to suppress the noise of the air flow as it enters and circulates through the first and second chambers 24, 34 by dampening much of the sound generated therein. Although only a pair of noise attenuating members 42 is illustrated in FIG. 6, it is pointed out that any number of noise attenuating members may be suitably positioned within the chambers 24, 34 including using only one member 42.

The third chamber portion 50 is positioned in flow communication with the first and second chamber portions 24, 34, and is bounded on opposite sides by the first and second filter members 26, 36 and receives the filtered air as it exits the first and second chamber portions 24, 34. The third chamber portion 50 is substantially open and is in flow communication with the outlet opening 54 preferably via an outlet region or outlet chamber portion 52 to provide an exit passageway for allowing the air which has passed through the filter members 26, 36 to exit the assembly for passage into the compressor assembly (not shown). The housing 12 includes partitions 28, 38 which separate the third chamber portion 50 from the outlet chamber portion 52. The upper side wall 28 extends substantially downwardly from the top surface or wall of the upper housing portion 16 and the lower side wall 38 extends substantially upwardly from the bottom surface or wall of the lower housing portion 14. The upper and lower side walls 28, 38 can mate with each other when the housing portions 14 and 16 are joined and form an opening 55 through which air exiting the third chamber portion 50 enters the outlet chamber portion 52. The size and shape of the opening 55 can likewise vary and it can take on a wide variety of different sizes and shapes depending upon the application. The outlet opening 54 includes a tubular extension 40 defining a portion thereof as illustrated in FIGS. 1, 2, 4 and 6. The tubular extension 40 is adapted for coupling to a corresponding compressor fitting to which the present filter assembly 10 would be attached. It is pointed out that the tubular extension 40 could be modified to be adapted for connection to any suitable type of compressor fitting depending upon the particular application involved. This means that the tubular portion 40 could be either internally or externally threaded based upon the particular compressor fitting, or a suitable hose or other fitting member could be slidably engaged over the exterior portion of tubular extension 40.

In the illustrated embodiment, another optional noise attenuating member 62 can be positioned and located in front of outlet opening 54 to further suppress the noise associated with the air flow as it passes through the third and outlet chamber portions 50 and 52 respectively and exits the housing 12. A suitable structure or other appropriate means, not shown, can be positioned within the lower housing portion 14 so as to sufficiently hold the noise attenuating member 62 in proper position in front of outlet opening 54. It is also recognized and anticipated that optional noise attenuating member(s) can likewise be positioned within the third chamber portion 50 if so desired.

As best shown in FIG. 2, the outlet chamber portion 52 is positioned adjacent to or in flow communication with the third chamber portion 50. As shown in FIG. 2, the third and outlet chamber portions 50, 52 can be separated by partition members 28, 38 or such chamber portions could be formed otherwise. The third and outlet chamber portions 50 and 52 can be considered as one chamber portion within the housing 12 with partitions 28, 38 therebetween. Although the noise attenuating members 62 function primarily to dampen the overall noise level of the air flow moving through the filter assembly 10, such members can also serve as an additional filtering medium as air flow will likewise move through these members as the ambient air flows its way through chamber portions 24, 34, 50 and 52.

Air exiting the first chamber portion 24 and second chamber portion 34 enters the third chamber portion 50 and flows its way through the outlet chamber portion 52. The tubular extension member 40 has the outlet opening 54 therein for allowing the air which is circulated through filter assembly 10 to exit the filter assembly for passage into the compressor assembly. The tubular extension member 40 is adapted for connection to any suitable type of compressor fitting depending upon the particular application involved. Sound wave reflections and reverberations are therefore dampened by the positioning and location of the noise attenuating members within the filter assembly 10, if used.

Figure 8:
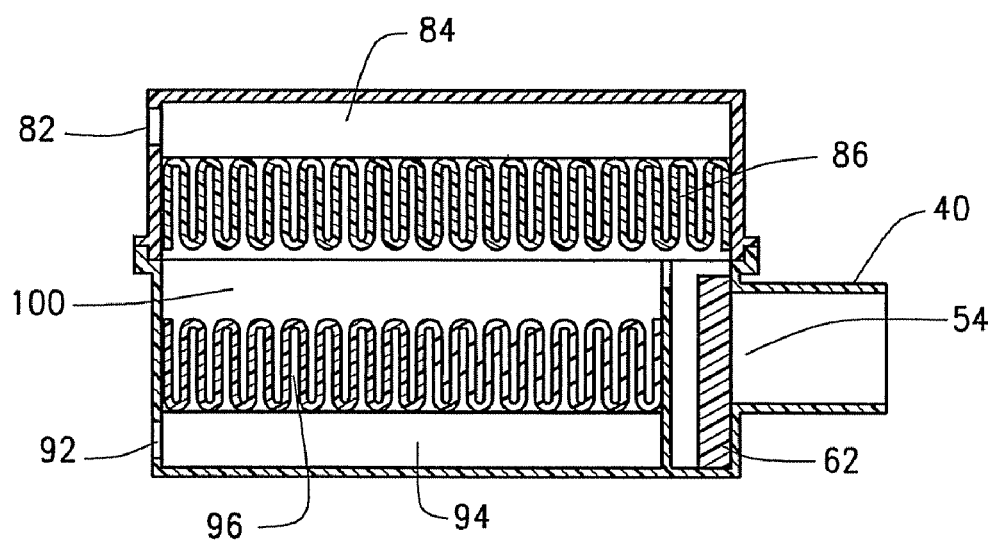
FIG. 8 is a cross-sectional view of the filter assembly of FIG. 7 taken along line 8-8 of FIG. 7.

FIGS. 7 and 8 disclose another embodiment 110 of the present filter assembly. The housing 112 is substantially similar in construction and operation to the housing 12 but differing therefrom in that the outlet chamber portion 52 associated with the filter assembly 10 has been modified from the filter assembly 110. Like the housing 12, the housing 112 includes an upper housing portion 116 and a lower housing portion 114 which, when sealed in an airtight fashion as previously explained, form first, second and third chamber portions 84, 94, 100. The wall defining the first chamber portion 84 includes at least one first inlet opening 82, the second chamber portion 94 includes at least one second inlet opening 92 and the third chamber portion 100 includes at least one outlet opening 54. The first chamber portion 84 is constructed substantially similar to the construction of chamber portion 24 associated with filter assembly 10 and includes a conventional first filter member 86 and may optionally include one or more noise attenuating members positioned adjacent the top portion of first filter member 86 as previously described with respect to filter assembly 10 (FIG. 6). The second chamber portion 94 is constructed substantially similar to the construction of the second chamber portion 34 and includes a conventional second filter member 96 and may likewise optionally include one or more noise attenuating members positioned adjacent the bottom portion of the second filter member 96 as previously described with respect to filter assembly 10 (not shown). Ambient air will enter the filter assembly 110 through the inlet openings 82, 92 and travels through the first and second chambers 84, 94 in a substantially similar manner as previously described with respect to the first and second chambers 24, 34.

Air exiting the first chamber portion 84 and second chamber portion 94 enters the third chamber portion 100 and flows its way through an optional noise attenuating member 62 positioned in front of and across the mouth of the outlet opening 54 for passage into the compressor assembly. The noise attenuating member 62 is held in proper position in front of outlet opening 54. A tubular extension member 40 communicates with the outlet opening 54 for allowing the air which is circulated through filter assembly 110 to exit the filter assembly for passage into the compressor assembly. The tubular extension member 40 is likewise adapted for connection to any suitable type of compressor fitting depending upon the particular application involved. As best shown in FIG. 8, the first filter member 86 extends substantially all the way to the respective opposite end walls of the upper housing portion 116 thereby providing more filtration surface area for air exiting the first inlet chamber 84 as compared to the second filter member 96. This configuration allows filter assembly 110 to provide more filtration surface area as compared to filter assembly 10.

The filter housing portions 14, 16, 114 and 116 can be made by injection molding plastic resin, although other materials and processes may likewise be utilized. Still further, the overall dimensions of the present filter assemblies as well as the specific shape and configuration of the various members associated therewith are also subject to wide variations and may be sized and shaped into a wide variety of different sizes and configurations so as to be compatible with the size and shape of the particular compressor assembly into which the present structures may be mounted, or to conform with any space limitations associated therewith out impairing the teachings and practice of the present invention. Although the filter assemblies 10 and 110 are illustrated as being substantially rectangular, such members can likewise take on other shapes such as square, triangular and so forth.

According to another embodiment of the present filter assembly, the filter assembly can be used to mix two different gases. A first gas entering the first inlet opening 22 will flow through the first chamber portion 24 and the first filter member 26 into the third chamber portion 50 and a second gas entering the second inlet 32 will flow through the second chamber portion 34 and the second filter member 36 into the third chamber portion 50 located adjacent to and on the opposite side of second filter member 36. The first and second gases entering the third chamber portion 50 are mixed in the third chamber portion 50.

Moreover, it will be understood that although the terms first, second and third are used herein to describe various features, elements, regions, layers and/or sections, these features, elements, regions, layers and/or sections should not be limited by these terms. These terms are only used to distinguish one feature, element, region, layer or section from another feature, element, region, layer or section. Thus, a first feature, element, region, layer or section discussed below could be termed a second feature, element, region, layer or section, without departing from the teachings of the present invention.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art.

Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow. The scope of the disclosure is not intended to be limited to the embodiments shown herein, but is to be accorded the full scope consistent with the claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A filter assembly for use with an air flow inducing medical device comprising:
   a housing having a plurality of inlet openings and at least one outlet opening;
   a first chamber portion located within said housing and being in flow communication with a first inlet opening for receiving ambient air therethrough;
   a second chamber portion located within said housing and being in flow communication with a second inlet opening for receiving ambient air therethrough;
   a third chamber portion located within said housing and being in flow communication with said outlet opening;
   a first filter member disposed inside said housing and separating said first chamber portion from said third chamber portion;
   a second filter member disposed inside said housing and separating said second chamber portion from said third chamber portion;
   an outlet chamber portion located within said housing in flow communication with said third chamber portion such that ambient air passing through said third chamber portion will enter said outlet chamber portion, said outlet chamber portion being in flow communication with said at least one outlet opening;
   a partition positioned between said third chamber and said outlet chamber, the partition forming an opening through which air exiting said third chamber portion enters said outlet chamber portion; and
   an extension member for being coupled to an air flow inducing medical device, the extension member extending from an outer surface of said housing, the extension member being in flow communication with said at least one outlet opening,
   wherein said first and second chamber portions are disposed at the opposite sides of said third chamber portion in the housing, said third chamber portion being disposed between the first filter member and the second filter member, and ambient air passing through said first and second filter members can exit through said third chamber portion into said outlet opening such that said at least one outlet opening is the only outlet opening of the filtered air and the only air path into said at least one outlet opening is through one of said first and second filter members.

2. The filter assembly defined in claim 1 wherein said first chamber portion being positioned in flow communication with a plurality of inlet openings for receiving ambient air therethrough.

3. The filter assembly defined in claim 1 wherein said second chamber portion being positioned in flow communication with a plurality of inlet openings for receiving ambient air therethrough.

4. The filter assembly defined in claim 1 further comprising at least one noise attenuating member positioned within said first chamber portion adjacent to at least a portion of one side of said first filter member, said noise attenuating member functioning as sound dampening means to dampen sound generated within the housing due to air flow passing therethrough.

5. The filter assembly defined in claim 1 further comprising at least one noise attenuating member positioned within said second chamber portion adjacent at least a portion of one side of said second filter member, said noise attenuating member functioning as sound dampening means to dampen sound generated within the housing due to air flow passing therethrough.

6. The filter assembly defined in claim 1 further comprising a noise attenuating member positioned across said outlet opening, said noise attenuating member functioning as sound dampening means to dampen sound generated within the housing due to air flow passing therethrough.

7. The filter assembly defined in claim 1 wherein said housing including a first housing portion and a second housing portion.

8. The filter assembly defined in claim 7 wherein said first housing portion including the first inlet opening and said second housing portion including the second inlet opening.

9. The filter assembly defined in claim 1 wherein said housing having a generally rectangular configuration.

10. The filter assembly defined in claim 1 wherein said filter members including HEPA filters.

11. A filter assembly for use with an air flow inducing medical device comprising:
    a housing having a plurality of inlet openings and at least one outlet opening;
    a first chamber portion located within said housing and being in flow communication with a first inlet opening for receiving ambient air therethrough;
    a second chamber portion located within said housing and being in flow communication with a second inlet opening for receiving ambient air therethrough;
    a third chamber portion located within said housing and being in flow communication with said outlet opening;
    a first filter member disposed inside said housing and being in flow communication with said first chamber portion;
    a second filter member disposed inside said housing and being in flow communication with said second chamber portion;
    an outlet chamber portion located within said housing in flow communication with said third chamber portion such that ambient air passing through said third chamber portion will enter said outlet chamber portion, said outlet chamber portion being in flow communication with said outlet opening;
    a partition positioned between said third chamber and said outlet chamber, the partition forming an opening through which air exiting said third chamber portion enters said outlet chamber portion; and an extension member for being coupled to an air flow inducing medical device, the extension member extending from an outer surface of said housing, the extension member being in flow communication with said at least one outlet opening, said first and second chamber portions, said first and second filter members and said third chamber portion being disposed within said housing such that ambient air entering said first inlet opening will flow from said first chamber portion through said first filter member into said third chamber, and through said third chamber portion into said outlet opening, and ambient air entering said second inlet opening will flow from said second chamber portion through said second filter member into said third chamber, and through said third chamber portion into said outlet opening such that said at least one outlet opening is the only outlet opening of the filtered air and the only air path into said at least one outlet opening is through one of said first and second filter members, wherein said first and second chamber portions are disposed at the opposite sides of said third chamber portion in the housing, said third chamber portion being disposed between the first filter member and the second filter member.

12. The filter assembly defined in claim 11 wherein said first chamber portion being positioned in flow communication with a plurality of inlet openings for receiving ambient air therethrough.

13. The filter assembly defined in claim 11 wherein said second chamber portion being positioned in flow communication with a plurality of inlet openings for receiving ambient air therethrough.

14. The filter assembly defined in claim 11 further comprising at least one noise attenuating member positioned within said first chamber portion adjacent at least a portion of one side of said first filter member, said noise attenuating member functioning as sound dampening means to dampen sound generated within the housing due to air flow passing therethrough.

15. The filter assembly defined in claim 11 further comprising at least one noise attenuating member positioned within said second chamber portion adjacent at least a portion of one side of said second filter member, said noise attenuating member functioning as sound dampening means to dampen sound generated within the housing due to air flow passing therethrough.

16. The filter assembly defined in claim 11 further comprising a noise attenuating member positioned across said outlet opening, said noise attenuating member functioning as sound dampening means to dampen sound generated within the housing due to air flow passing therethrough.

17. The filter assembly defined in claim 11 wherein said housing includes a first housing portion and a second housing portion.

18. The filter assembly defined in claim 17 wherein said first housing portion includes the first inlet opening and said second housing portion includes the second inlet opening.

19. The filter assembly defined in claim 11 wherein said housing having a generally rectangular configuration.

20. The filter assembly defined in claim 11 wherein said filter members including HEPA filters.

* * * * *